United States Patent [19]

Ali

[11] Patent Number: 4,621,635

[45] Date of Patent: Nov. 11, 1986

[54] METHOD FOR TREATING HEMORRHOIDS

[75] Inventor: Max Ali, Belleville, Mich.

[73] Assignee: Hemorrhoid Clinic of America, Oak Park, Mich.

[21] Appl. No.: 827,831

[22] Filed: Feb. 7, 1986

[51] Int. Cl.⁴ .............................................. A61B 17/30
[52] U.S. Cl. .................................. 128/303.1; 128/401
[58] Field of Search .................... 128/303.1, 395–403, 128/DIG. 27

[56] References Cited

U.S. PATENT DOCUMENTS

| | | | |
|---|---|---|---|
| 3,939,842 | 2/1976 | Harris | 128/401 |
| 4,142,529 | 3/1979 | Latenser et al. | 128/401 |
| 4,211,231 | 7/1980 | Rzasa | 128/303.1 |
| 4,227,535 | 10/1980 | Connor | 128/401 |
| 4,240,436 | 12/1980 | Singleton | 128/401 |
| 4,266,547 | 5/1981 | Komiya | 128/303.1 |
| 4,331,151 | 5/1982 | Golden | 128/400 |
| 4,538,609 | 9/1985 | Takenaka et al. | 128/303.1 |
| 4,563,182 | 1/1986 | Stoy et al. | 128/401 |

FOREIGN PATENT DOCUMENTS

| | | | |
|---|---|---|---|
| 2416881 | 3/1976 | Fed. Rep. of Germany | 128/401 |
| 3119322 | 1/1983 | Fed. Rep. of Germany | 128/303.1 |
| 2240745 | 3/1975 | France | 128/401 |
| 516216 | 5/1977 | U.S.S.R. | 128/303.1 |

Primary Examiner—Edward M. Coven
Assistant Examiner—Max F. Hindenburg
Attorney, Agent, or Firm—Cullen, Sloman, Cantor, Grauer, Scott & Rutherford

[57] ABSTRACT

A method of treating external hemorrhoids comprises the preliminary and optional step of rubber band ligation of any associated internal hemorrhoidal tissue, followed by a laser beam-created incision around the perimeter of the base of the external portion. The surface of the external portion is then evaporated with a traversing movement of the laser beam. The laser beam is then employed to form a cavity into the core of the hemorrhoid, dimensioned to accommodate the subsequent insertion of a cryogenic probe, which freezes the hemorrhoidal tissue from the interior outwardly.

5 Claims, 4 Drawing Figures

METHOD FOR TREATING HEMORRHOIDS

BACKGROUND OF THE INVENTION

The present invention relates to an improved technique for treatment of hemorrhoids. A number of techniques have been employed in the past, including surgical excision, banding and cryosurgery.

In the rubber band ligation technique, a specially designed proctoscope functions as the drum of a ligator and carries a rubber band around its tip. The hemorrhoid is then drawn into the proctoscope by forceps, and the band slipped off the tip of the proctoscope onto the neck of the hemorrhoid. The rubber band cuts off the blood supply to the hemorrhoidal tissue, resulting in necrosis. The banding technique can only be used for internal hemorrhoids, located above (i.e., internally of) the pectinate line which divides the more externally located somatic nervous system from the more internally located zone of the autonomic nervous system which does not carry pain sensations.

The cryosurgical technique involves the application of a probe which is at sub-zero necrosis-producing temperature to the surface of the hemorrhoidal tissue. Carbon dioxide or nitrous oxide is used as a refrigerant in such tools. The gas is supplied under pressure to the tip of the probe, where expansion of the gas causes a rapid removal of heat from the tip of the probe. Heat is similarly rapidly removed, by conduction, from the target tissue to which the probe has been applied.

While lasers have been described for treatment of venereal warts in the rectum, which are very small lesions as compared with the tissue mass of a hemorrhoid, lasers have not to Applicant's knowledge been suggested for treatment of hemorrhoids. Furthermore, it is difficult to use a laser on interior hemorrhoids, because the need to work through a proctoscope makes access and proper focusing of the beam difficult.

While the separate use of the banding and cryosurgery techniques described above have achieved adequate success in some cases, they have been unsuccessful in others. It is the primary purpose of the present invention to provide an improved method of treating hemorrhoids, which method is safe and capable of achieving a high rate of success.

SUMMARY OF THE INVENTION

According to the present invention, the cryosurgery technique is modified to cause freezing of the hemorrhoidal tissue from the inside out, rather than from the surface inward. This technique produces more effective and complete freezing, thereby causing obstruction of the blood vessels supplying the hemorrhoidal tissue and resulting in complete necrosis.

If the hemorrhoidal tissue includes an internal portion, that portion is defined and banded according to conventional procedures. Next, an incision is made around the base of the external portion of the hemorrhoid using a laser beam to cut off the cutaneous blood supply, thereby causing necrosis of the covering skin. This incision is preferably one to two millimeters deep. Then, the laser beam is traversed with a scanning motion across the entire surface of the external hemorrhoid to evaporate that tissue to a depth of approximately one millimeter. This denudes the hemorrhoid of its protective outer skin, which has its own blood supply, and further assures complete necrosis.

Next, as a preliminary to the unique freezing procedure of the present invention, the laser beam is utilized to form by evaporation a cavity in the external hemorrhoidal mass, the cavity preferably being five to ten millimeters in depth and about five millimeters in diameter. Depending upon the size of the external hemorrhoid, anywhere from one to three such cavities may be created. Finally, the cryogenic probe is inserted directly into the laser-formed cavities, to freeze the hemorrhoidal mass from the inside out. This step normally requires that the probe be retained within the cavity for two to five minutes.

It is to be understood that the preliminary step of banding is optional, being utilized only where there is internal as well as external hemorrhoidal tissue.

DETAILED DESCRIPTION OF THE INVENTION

Figure 1:
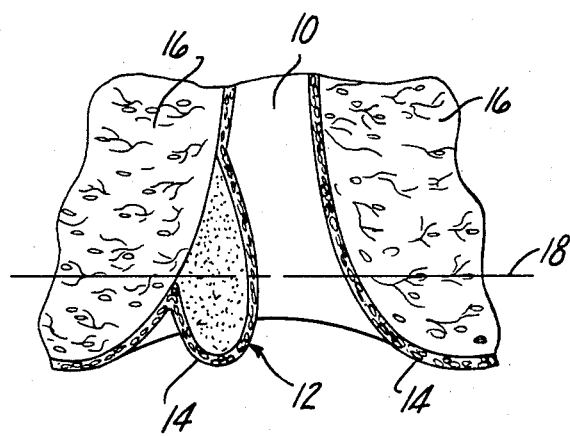
FIG. 1 is a cross-sectional view of a rectum including a hemorrhoid having internal as well as external portions.

FIG. 1 shows in cross-section the outer portion of the rectum 10 of a patient having an external-internal hemorrhoid 12. The skin is shown at 14 and the normal subcutaneous tissue is shown at 16. Pectinate line 18 separates the outer zone supplied by the somatic nervous system from the inner zone which is supplied by the autonomic nervous system. As is well known, the banding technique, to be described below, is too painful for use outside the pectinate line, but is appropriate for use internally of that line, where the autonomic nervous system does not carry the sensation of pain.

Figure 2:
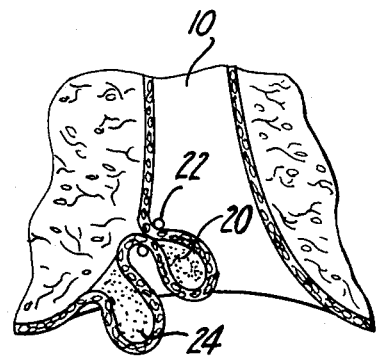
FIG. 2 is a view similar to FIG. 1, after application of a rubber band to the internal portion of the hemorrhoid.

If, as shown in the figures, the hemorrhoidal mass extends significantly into the interior of the rectum, it is preferred to initially isolate the internal portion and treat it in conventional fashion by rubber band ligation. Because that technique is conventional, it will not be further described here, other than to state that FIG. 2 of the drawings shows the hemorrhoid after the internal portion 20 has been ligated by rubber band 22. The method of treatment according to the present invention requires no further treatment of internal hemorrhoid 20, which will suffer gradual necrosis in the usual fashion. The ligating step then leaves for further treatment external hemorrhoid 24, as will be described below.

The next steps involve the use of a laser beam, both as a cutting and as a tissue-evaporating means. Applicant has successfully used a Cavitron 300A carbon dioxide laser, manufactured by Laser Sonics, with approximately 15 to 25 watts of power. Initially, the finely focused beam is used as a light scalpel to make a circumferential incision around the perimeter of the base of external hemorrhoid 24, the incision being preferably about one to two millimeters deep. This incision cuts off the cutaneous blood supply, causes necrosis of the skin.

Figure 3:
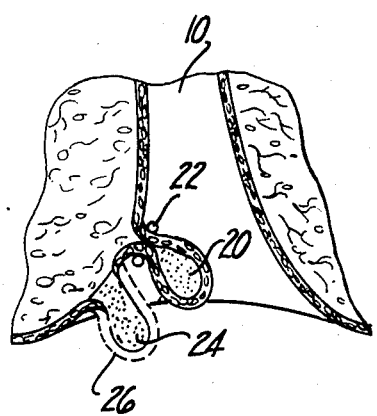
FIG. 3 is a view similar to FIG. 2, showing in dotted lines the portion of the external hemorrhoid which has been evaporated by a scanning motion of the laser beam.

Next, the less sharply focused beam is traversed back and forth across the entire surface of external hemorrhoid 24, evaporating the outer one millimeter of protective skin, the portion thus removed being shown at 26 in FIG. 3. This step further assures necrosis of the skin.

Figure 4:
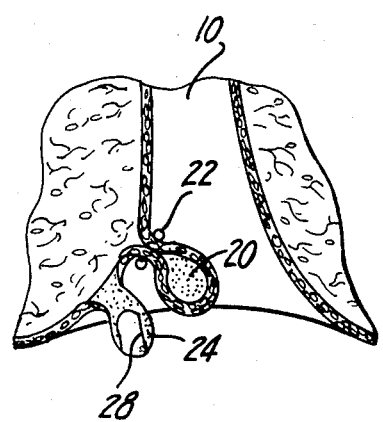
FIG. 4 is a view similar to FIG. 3, following creation of a cavity by the laser beam.

The final pre-cryosurgery step is to utilize the beam to form a core or cavity in the central mass of the external hemorrhoid, as shown at 28 in FIG. 4. The purpose of the cavity is to permit access of the cryogenic probe deep into the interior of the hemorrhoid. Therefore, it is preferred that the cavity be five to ten millimeters deep, and approximately five millimeters in diameter. A large external hemorrhoid may require up to three of such cavities to assure complete exposure of the core of the hemorrhoid to destructively freezing temperature.

Applicant has utilized a Cryomedic MT 600 cryogenic device, utilizing nitrous oxide gas, for this unique treatment. The probe is inserted into each of cavities 28, preferably for a period of two to five minutes to assure adequate necrosis. The tip reaches a temperature of $-65°$ to $-89°$ C. Human tissue freezes at $-2.2°$ C., but actual tissue destruction begins at $-10°$ to $-20°$ C. As freezing progresses, an ice ball can be seen forming laterally as a halo around the probe tip. However, the outer edge of the ice ball only reaches a temperature of $0°$ C., and therefore ice ball formation should be allowed to progress beyond the border of the area to be treated, to achieve adequate necrosis of the target tissue.

The above-described technique, by which freezing progresses outwardly from the core of the hemorrhoid, rather than from the surface inward, is believed to be more effective. A probable basis for the improved results is that the blood supply is destroyed closer to its source, rather than at its terminal end.

This invention may be further developed within the scope of the following claims. Accordingly, the above specification is to be interpreted as illustrative of only a single operative embodiment of the present invention, rather than in a strictly limited sense.

I now claim:

1. A method for treating hemorrhoids comprising the steps of:
    (a) evaporating the outer surface of a hemorrhoid by traversing such surface with a scanning motion of a laser beam;
    (b) forming at least one cavity in such hemorrhoid by the application of the laser beam thereto to a depth sufficient to reach the approximate core thereof and to a diameter adequate to permit reception therein of a cryogenic probe; and
    (c) freezing such hemorrhoid outwardly from its interior by inserting a cryogenic probe into each such cavity for a time sufficient to assure complete necrosis of the hemorrhoidal mass.

2. The method of claim 1 which further includes the step of making a shallow incision with the laser beam around the circumference of the hemorrhoid to devascularize the skin covering the hemorrhoidal mass.

3. The method of claim 1 wherein said cavities are formed to a depth of about five to ten millimeters and a diameter of about four to six millimeters.

4. A method for treating a hemorrhoidal mass having portions extending both internally and externally of the rectum comprising the steps of:
    (a) applying a rubber band to the internal portion of the hemorrhoid to segregate and strangulate such portion;
    (b) evaporating the outer surface of the external portion of the hemorrhoid by traversing such surface with a scanning motion of a laser beam;
    (c) forming at least one cavity in said external portion to a depth of about five to ten millimeters and a diameter of about four to six millimeters by the application of the laser beam thereto; and
    (d) freezing the external portion of the hemorrhoid by inserting a cryogenic probe into each such cavity for a time sufficient to assure complete necrosis of the external hemorrhoidal mass.

5. The method of claim 4 which further includes the step of making a shallow incision with the laser beam around the circumference of the external hemorrhoid to devascularize the skin covering the external hemorrhoidal mass.

* * * * *